United States Patent [19]
Strittmatter et al.

[11] Patent Number: 5,811,243
[45] Date of Patent: Sep. 22, 1998

[54] METHODS AND COMPOSITIONS FOR BINDING TAU AND MAP2C PROTEINS

[75] Inventors: Warren J. Strittmatter; Allen D. Roses, both of Durham, N.C.; Michel Goedert, Cambridge, England; Karl H. Weisgraber, Walnut Creek, Calif.; Ann M. Saunders; Donald E. Schmechel, both of Durham, N.C.

[73] Assignee: Duke University, Durham, N.C.

[21] Appl. No.: 740,232

[22] Filed: Oct. 25, 1996

Related U.S. Application Data

[60] Division of Ser. No. 287,218, Aug. 8, 1994, which is a continuation-in-part of Ser. No. 114,910, Aug. 31, 1993, abandoned.

[51] Int. Cl.$^6$ ............................. C12Q 1/00; G01N 33/53; C07K 14/00
[52] U.S. Cl. .............................................. 435/7.1; 530/350
[58] Field of Search ................................ 530/350; 435/7.1

[56] References Cited

PUBLICATIONS

Moraga et al 1992 Biochim. Biophys. Acta 1121 (1–2) 97–103 Abstract only.
Strittmatter et al 1994 PNAS 91:11183–11186.

*Primary Examiner*—Karen Carlson
*Attorney, Agent, or Firm*—Myers Bigel Sibley & Sajovec, P.A.

[57] ABSTRACT

A method of combatting Alzheimer's disease which comprises increasing the binding of the tau protein in nerve cells of that subject, and/or the binding of MAP2c protein in nerve cells of that subject, to either Apolipoprotein E or an Apolipoprotein E fragments capable of binding tau and/or MAP2c. In one embodiment, the method comprises administering the ApoE or ApoE fragment to the subject; in another embodiment, the method comprises administering to the subject a vector capable of entering nerve cells, which vector then upregulates the expression of an ApoE or an ApoE fragment capable of binding tau and/or MAP2c in nerve cells. Compositions useful for carrying out these methods are also disclosed.

6 Claims, 7 Drawing Sheets

METHODS AND COMPOSITIONS FOR BINDING TAU AND MAP2C PROTEINS

RELATED APPLICATIONS

This application is a divisional of Ser. No. 08/287,218, filed Aug. 8, 1994, which is a continuation-in-part of application Ser. No. 08/114,910, filed Aug. 31, 1993, now abandoned.

This invention was made with Government support under NIH LEAD Award 5R35 AG-07922 and NIH Alzheimer's Disease Research Center Award 5P50 AG-05128 and Grant No. HL41633 awarded by the National Institutes of Health. The Government has certain rights to this invention.

FIELD OF THE INVENTION

The present invention concerns methods of binding tau protein in cells, methods of binding MAP2 protein in cells, methods of inhibiting neurofibrillary tangle formation, methods of combatting Alzheimer's disease by binding tau protein to either an Apolipoprotein E or an Apolipoprotein E fragment which binds to tau, and methods of combatting Alzheimer's disease by binding MAP2c protein to either an Apolipoprotein E or an Apolipoprotein E fragment which binds to MAP2c protein.

BACKGROUND OF THE INVENTION

Apolipoprotein E exists in humans in three different isoforms. These isoforms are known as apolipoprotein E2, apolipoprotein E3, and apolipoprotein E4 (abbreviated ApoE2, ApoE3, and ApoE4, respectively). ApoE3 is the most common isoform in the general population, and contains a single cysteine at residue 112. ApoE4 contains an arginine at this position, but is otherwise identical to ApoE3.

ApoE4 is genetically associated with late-onset familial and sporadic Alzheimer's disease. See, e.g., W. Strittmatter et al., Proc. Natl. Acad. Sci. USA 90, 1977 (1993)). The allele frequency of ApoE4 is highly statistically increased in patients in late-onset Alzheimer's disease families. Moreover, in a series of 176 autopsy confirmed late-onset sporadic Alzheimer's disease patients, the allele frequency of ApoE4 was also markedly elevated. Furthermore, the risk of Alzheimer's disease is increased as a function of the inherited dose of ApoE4, and the mean age of onset is lowered with each ApoE4 allele. By age 80 years, virtually all individuals who are homozygous for ApoE4 will develop Alzheimer's disease. See E. Corder et al., Science 261, 921 (1993). Thus the disease is inherited as a co-dominant trait, and manifested when individuals live long enough to be at risk. This work provides an important diagnostic and prognostic tool for identifying Alzheimer's disease patients, or persons at risk for developing Alzheimer's disease. However, it does not directly indicate an underlying cause for Alzheimer's disease.

Alzheimer's disease is accompanied by the formation of neurofibrillary tangles and by the deposition of amyloid beta-peptide (AP). Dementia in Alzheimer's disease is generally accepted to be better correlated with the neurofibrillary tangle pathology than with the extent of AB deposition. These neurofibrillary tangles contain paired helical filaments whose principal constituent is abnormally phosphorylated tau (Ptau), a microtubule-associated protein. However, the precise reason for the accumulation of Ptau and the consequent formation of neurofibrillary tangles has not been known.

The microtubule-associated protein MAP2c also effects microtubule assembly and stability. Tau and MAP2 are both members of a family of neuronal microtubule-associated proteins (MAPS) which promote microtubule assembly and stabilize microtubules.

Both Tau and MAP2 proteins contain a highly conserved microtubule-binding repeat region although the repeat region of each differs in sequence (see Lewis et al., Science, 242, 936 (1988); Bulinski, MAP4, in: Microtubules, Hyams and Lloyd (Eds.), Wiley-Liss, New York, P. 167–182 (1994)). MAP2c is a 70 kDa form of MAP2 arising from alternative mRNA splicing of the MAP2 gene (Garner and Matus, J. Cell. Biol., 106, 779 (1988)). Like other forms of MAP2, MAP2c contains three or four copies of the microtubule-binding repeats, which are highly homologous to the microtubule-binding repeats of tau.

V. Ingram and H. Roder, PCT Application WO 93/03148, describe the use of inhibitors of the kinases PK40 and PK36 (e.g., ATP) to inhibit the formation of paired helical filaments in cells, to inhibit the formation of neurofibrillary tangles in cells, and to treat Alzheimer's disease in patients.

C. Preston and I. Ace, PCT Application WO 91/02788, describe the administration of nerve growth factor beta subunit by a herpes simplex virus type 1 mutant for the treatment of Alzheimer's disease.

SUMMARY OF THE INVENTION

The present invention is based on the finding that ApoE3 binds avidly to the tau protein but ApoE4 does not, that neither ApoE3 nor ApoE4 binds to phosphorylated tau, and that ApoE3 binds avidly to the MAP2c protein but ApoE4 does not. Thus, the present invention provides a method of inhibiting the formation of paired helical filaments and/or neurofibrillary tangles in a cell by administering to (or introducing into) the cell either an apolipoprotein E which binds to tau (e.g., ApoE2, ApoE3), or an apolipoprotein E fragment which binds to tau in that cell. Administration may be carried out by either delivering the active agent directly to the cell, or by delivering genetic material to the cell which in turn delivers the active agent to the cell.

A second aspect of the present invention is a method of combatting the formation of neurofibrillary tangles and/or Alzheimer's disease in a subject in need of such treatment by administering to the subject an ApoE which binds to tau, or a fragment thereof which binds to tau.

A third aspect of the present invention is a pharmaceutical formulation comprising an ApoE which binds to tau, or a fragment thereof which binds to tau (i.e., "the active agent") in a pharmaceutically acceptable carrier. Preferably the carrier is one which carries the active agent through the blood-brain barrier. Thus, the present invention provides for the use of an active agent as given above for the preparation of a medicament for combatting the formation of neurofibrillary tangles and/or combatting Alzheimer's disease.

A fourth aspect of the present invention is a method of combatting Alzheimer's disease in a subject in need of such treatment, comprising administering to the subject an active agent selected from the group consisting of apolipoprotein E which binds to microtubule associated protein 2c (MAP2c) and Apolipoprotein E fragments which bind to MAP2c in an amount effective to combat Alzheimer's disease in the subject.

A fifth aspect of the present invention is a pharmaceutical formulation useful for combatting Alzheimer's disease, comprising an active agent selected from the group consisting of ApoE which binds to MAP2c and fragments thereof which bind to MAP2c, in combination with a pharmaceutically acceptable carrier.

A particular embodiment of the present invention is, as noted above, a method of combatting the formation of neurofibrillary tangles and/or Alzheimer's disease in a subject in need of such., treatment by administering to the subject a vector capable of entering nerve cells. The vector may be either (a) a vector which carries a nucleic acid encoding an ApoE which binds tau or microtubule associated protein 2c (MAP2c), or a fragment thereof which binds tau or MAP2c, which nucleic acid is operably associated with a promoter which expresses the nucleic acid in a nerve cell; or (b) a vector containing a nucleic acid which is capable of converting the codon of the ApoE gene encoding the amino acid at residue 112 therein to cysteine in a nerve cell (e.g., to convert the ApoE4 gene to the ApoE3 gene in vivo by converting the codon encoding arginine to cysteine at residue 112).

Also disclosed herein is a vector as described above, pharmaceutical formulations containing such a vector, and the use of such vectors for the preparation of a medicament for combatting the formation of neurofibrillary tangles and/or Alzheimer's disease in a subject in need of such treatment.

The foregoing and other objects and aspects of the present invention are explained in detail in the drawings herein and the specification set forth below.

DETAILED DESCRIPTION OF THE INVENTION

Figure 1:
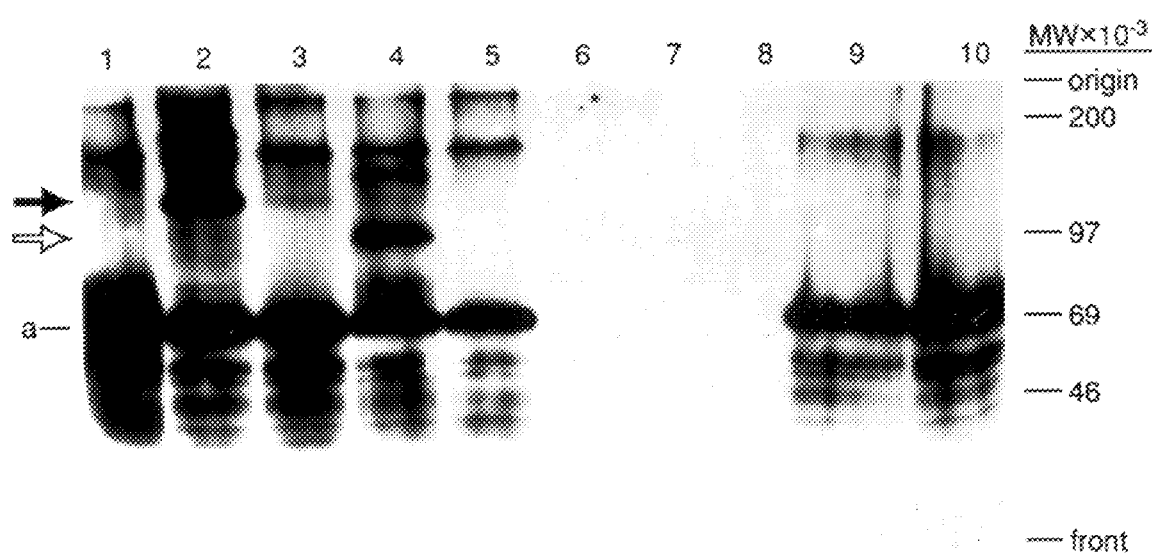
FIG. 1 illustrates the binding of the tau protein to ApoE3.

Cells treated by the method of the present invention are typically mammalian cells (e.g., human, dog, cat, rat, mouse), and are typically nerve cells. The nerve cells may be nerve cells of the central nervous system or the peripheral nervous system. The cells may be treated in vitro or in vivo in an animal host. The method is useful in analyzing the contribution of tau phosphorylation to cell maintenance, as well as in analyzing the contribution of tau phosphorylation, paired helical filament formation, and/or neurofibrillary tangle formation to neurocellular degeneration, both in vitro and in vivo. The method is also useful in analyzing the contribution of MAP2c protein to neurocellular degeneration, both in vitro and in vivo.

Suitable subjects for carrying out the present invention are typically male or female human subjects, and include both those which have previously been determined to be at risk of developing Alzheimer's disease, and those who have been initially diagnosed as being afflicted with Alzheimer's disease. For example, patients diagnosed or determined to be afflicted with dementia, particularly patients who had previously been clinically normal who are determined to be afflicted with a progressive dementia, are suitable subjects. The present invention may be employed in combating both familial Alzheimer's disease (late onset and early onset) as well as sporadic Alzheimer's disease. One preferable group of subjects are those who have been determined to be heterozygous or homozygous for the ApoE4 gene. Procedures for selecting and assessing subjects are further discussed in A. Roses, W. Strittmatter, G. Salvensen, J. Enghild and D. Schmichel, Methods of Detecting Alzheimer's Disease, U.S. patent application Ser. No. 08/114,448, filed Aug. 31, 1993 (attorney docket no. 5405-75A), which is a continuation-in-part of A. Roses et al., U.S. patent application Ser. No. 07/959,992 (filed Oct. 13, 1992) (the disclosures of which are incorporated by reference herein in their entirety)(see also W. Strittmatter et al., Proc. Natl. Acad. Sci. USA 90, 1977 (1992); E. Corder et al., Science 261, 921 (1993)).

The terms "combat" or "combatting", as used herein, are not intended to indicate a reversal of paired helical filament formation, neurofibrillary tangle formation, or the Alzheimer's disease process, but are instead intended to indicate a slowing of these events, such as a delaying of onset of dementia or a slowing of the progression of dementia. Thus, the method of the present invention may be carried out either therapeutically in a patient where initial signs of Alzheimer's disease are present, or prophylactically in a subject at risk of developing Alzheimer's disease.

ApoE2, ApoE3, and fragments thereof which bind to tau protein and/or to MAP2c protein ("active agents") may be produced by standard techniques. Fragments employed in carrying out the present invention may be peptides derived from ApoE which have N-terminal, C-terminal, or both N-terminal and C-terminal amino acid residues deleted, but retain the biological activity of the parent protein as described herein (e.g., preferably retain a cysteine at the position in the fragment corresponding to position 112 of the complete ApoE2 or ApoE3 protein, and bind tau at the site bound by complete ApoE3), and bind MAP2c at the site bound by complete ApoE3. Examples of such fragments that bind tau include ApoE3 fragments 1–191, 1–244, 1–266, and 1–272 (where 1 refers to the N-terminal amino acid of the native molecule). Such active fragments may be prepared by enzymatic digestion of an ApoE (particularly ApoE2 or ApoE3), by direct synthesis, or by genetic engineering procedures. Methods to assess the binding of such fragments to tau or to MAP2c will be readily apparent to those in the art. It will also be readily apparent that some fragments may be able to bind both tau and MAP2c proteins.

The terms ApoE (e.g., ApoE2, ApoE3) and ApoE fragments as employed are intended to include the analogs thereof. An "analog" is a chemical compound similar in structure to another which has a similar physiological action (e.g., another peptide). Such analogs may initially be prepared by adding, altering or deleting amino acids. For example, from 1 to 5 additional amino acids may be added to the N-terminal, C-terminal, or both the N-terminal and C-terminal of an active fragment. In another example, one or more amino acids of a synthetic peptide sequence may be replaced. by one or more other amino acids which does not affect the activity of that sequence. Analogs may also be small organic compounds which mimic or have the activity of the parent compound such as ApoE3 as described herein (e.g., bind to the tau protein at the binding site bound by ApoE3). Changes in the parent compound to construct the analog can be guided by known similarities between amino acids and other molecules or substituents in physical features such as charge density, hydrophobicity, hydrophilicity, size, and configuration, etc. For example, Thr may be replaced by Ser and vice versa, Asp may be replaced by Glu and vice versa, and Leu may be replaced by Ile and vice versa. Further, the selection of analogs may be made by mass screening techniques known to those skilled in the art (e.g., screening for compounds which bind to the binding site on the tau protein bound by ApoE3).

Active agents of the present invention may be administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of a carboxylic acid group.

The amount of active agent administered to a subject will vary depending upon the age, weight, and condition of the subject, the particular active agent being delivered, the delivery schedule, and other such factors, but is generally from 0.1 nanograms to 100 micrograms, and is typically an amount ranging from 1 nanogram to 10 micrograms.

Pharmaceutical compositions containing the active agents of the present invention may be prepared in either solid or liquid form. To prepare the pharmaceutical compositions of this invention, one or more of the active agents is intimately admixed with a pharmaceutical carrier according to conventional pharmaceutical compounding techniques, which carrier may take a wide variety of forms depending on the form of preparation desired for administration, e.g. oral or parenteral (e.g., intravenous, subcutaneous, intrathecal). In preparing the compositions in oral dosage form, any of the usual pharmaceutical media may be employed. Thus, for liquid oral preparation, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterally injectable compositions, the carrier will usually comprise sterile, pyrogen-free water, or sterile, pyrogen-free physiological saline solution, though other ingredients, for example, for purposes such as aiding solubility or for preservatives, may be included. Parenterally injectable suspensions (e.g., for intravenous or intrathecal injection) may also be prepared, in which case appropriate liquid carriers, suspending agents and the like may be employed.

When necessary, the pharmaceutical composition may be prepared so that the active agent passes through the blood-brain barrier. One way to accomplish transport across the blood-brain barrier is to couple or conjugate the active agent to a secondary molecule (a "carrier"), which is either a peptide or a non-proteinaceous moiety. The carrier is selected such that it is able to penetrate the blood-brain barrier. Examples of suitable carriers are pyridinium, fatty acids, inositol, cholesterol, and glucose derivatives. Alternatively, the carrier can be a compound which enters the brain through a specific transport system in brain endothelial cells, such as transport systems for transferring insulin, or insulin-like growth factors I and II. This combination of active agent and carrier is called a prodrug. Upon entering the central nervous system, the prodrug may remain intact or the chemical linkage between the carrier and active agent may be hydrolyzed, thereby separating the carrier from the active agent. See generally U.S. Pat. No. 5,017,566 to Bodor (applicants specifically intend that the disclosure of this and all other U.S. patent references cited herein be incorporated herein in their entirety).

An alternative method for transporting the active agent across the blood-brain barrier is to encapsulate the carrier in a lipid vesicle such as a microcrystal or liposome. Such lipid vesicles may be single or multi-layered, and encapsulate the active agent either in the center thereof or between the layers thereof. Such preparations are well known. For example, PCT Application Wo 91/04014 of Collins et al. describes a liposome delivery system in which the therapeutic agent is encapsulated within the liposome, and the outside layer of the liposome has added to it molecules that normally are transported across the blood-brain barrier. Such liposomes can target endogenous brain transport systems that transport specific ligands across the blood-brain barrier, including but not limited to, transferring insulin, and insulin-like growth factors I and II. Alternatively, antibodies to brain endothelial cell receptors for such ligands can be added to the outer liposome layer. U.S. Pat. No. 4,704,355 to Bernstein describes methods for coupling antibodies to liposomes.

Another method of formulating the active agent to pass through the blood-brain barrier is to prepare a pharmaceutical composition as described above, wherein the active agent is encapsulated in cyclodextrin. Any suitable cyclodextrin which passes through the blood-brain barrier may be employed, including β-cyclodextrin, γ-cyclodextrin, and derivatives thereof. See generally U.S. Pat. No. 5,017,566 to Bodor; U.S. Pat. No. 5,002,935 to Bodor; U.S. Pat. No. 4,983,586 to Bodor.

Another method of passing the active agent through the blood-brain barrier is to prepare and administer a pharmaceutical composition as described above, with the composition further including a glycerol derivative as described in U.S. Pat. No. 5,153,179, the disclosure of which is incorporated herein by reference.

In an alternate embodiment, the present invention is carried out by administering to the subject a vector carry a nucleic acid active agent, which vector is capable of entering nerve cells. Such vectors may be formulated with pharmaceutical carriers and administered in like manner as described above. Suitable vectors are typically viral vectors, including DNA viruses (wherein the nucleic acid active agent is DNA) and RNA viruses, or retroviruses (wherein the nucleic acid active agent is RNA). It is preferred, but not essential, that the vector be a neurotropic vector which preferentially infects nerve cells. Techniques for carrying out gene therapy are known. See, e.g., T. Friedmann, Progress Toward Human Gene Therapy, Science 244, 1275 (1989); I. Pastan, U.S. Pat. No. 5,166,059.

Methods for passing genetic material through the blood-brain barrier, particularly viral or retroviral encapsidated material, are described in U.S. Pat. No. 4,866,042 to Neuwelt, the disclosure of which is incorporated herein by reference.

Herpesvirus vectors (e.g., herpesvirus type 1, herpesvirus type 2, cytomegalovirus) are a particular type of vector which may be employed to carry out the present invention. Herpes simplex virus type 1 (HSV-1) vectors are particularly preferred. Such vectors generally comprise at least the encapsidation segments of an HSV-1 DNA genome in an HSV-1 viral capsid. The HSV-1 DNA carries a heterologous DNA insert which either contains the active agent DNA molecule, or contains the DNA molecule which encodes the peptide or protein to be expressed. Where the insert DNA molecule encodes a protein or peptide, the insert is under the control of a promoter operative in nerve cells so that the protein or peptide is expressed in nerve cells. The promoter may be of any suitable origin, including of viral origin (e.g., promoters which control the latency-associated transcripts (LAT-s) of HSV-1; the HSV-1 immediate early 4/5 promoter), and promoters which are normally operable in mammalian nerve cells (e.g., the tau protein promoter). The heterologous insert is typically inserted into any region of the viral genome which is non-essential for culture of the virus to enable the production thereof in cell culture, and if necessary in helper cells. Such herpesvirus vectors are known. See, e.g., A. Geller and X. Breakefield, Science, pg 1667 (23 Sept. 1988); C. Ace et al., J. Virol. 63, 2260 (1989); C. Preston et al., PCT Application WO 91/02788.

A promoter is not essential for homologous recombination strategies. In such strategies, instead of a DNA to be expressed, the heterologous insert comprises a DNA molecule which is capable of converting the codon of the ApoE gene encoding the amino acid at residue 112 therein to cysteine in a nerve cell by homologous recombination. The DNA molecule is typically from 50 or 100 to 300 or 5,000 nucleotides in length, and is sufficiently homologous to the targeted chromosomal ApoE4 DNA to anneal to the complementary strand thereof and exchange with the portion of the chromosomal DNA segment which contains the codon encoding ApoE4 amino acid residue 112 by homologous recombination, thereby converting the codon encoding residue 112 to one encoding cysteine. Homologous recombination procedures are known.

See, e.g., 0. Smithies, Nature 317, 230 (1985); W. Bertling, U.S. Pat. No. 4,950,599.

Also disclosed herein is a method of screening compounds for the ability to achieve one or more of the effects of binding tau, inhibiting tau phosphorylation, inhibiting the formation of paired helical filaments, inhibiting the formation of neurofibrillary tangles, and combatting Alzheimer's disease. Such a method comprises contacting a test compound to the tau protein, and then detecting whether the test compound binds to the binding site on tau which is bound by ApoE3. The format of the assay and the manner by which the contacting step is carried out is not critical, and a variety of possibilities will be readily apparent to those skilled in the art. Typically, the contacting step is carried out in vitro, in an aqueous solution, and the detecting step is carried out by means of a competitive binding assay in which a known compound which binds to the ApoE3 binding site on tau, such as described above, is included in the solution, and the ability of the test compound to inhibit the binding of the known compound is determined. For such assays, the known compound is labelled with a suitable detectible group, such as tritium. Other assays, such as gel mobility shift assays, may also be employed. The presence of binding to the site bound by ApoE3 indicates the compound is or may be useful for achieving one or more of the effects noted above. Compounds detected in this manner are useful for the in vitro and in vivo study of tau phosphorylation, paired helical filament formation, neurofibrillary tangle formation, and the treatment of Alzheimer's disease.

Also disclosed herein is a method of screening compounds for the ability to achieve one or more of the effects of binding MAP2c and combatting Alzheimer's disease. Such a method comprises contacting a test compound to the MAP2c protein, and then detecting whether the test compound binds to the binding site on MAP2c which is bound by ApoE3. The format of the assay and the manner by which the contacting step is carried out is not critical, and a variety of possibilities will be readily apparent to those skilled in the art. Typically, the contacting step is carried out in vitro, in an aqueous solution, and the detecting step is carried out by means of a competitive binding assay in which a known compound which binds to the ApoE3 binding site on MAP2c, such as described above, is included in the solution, and the ability of the test compound to inhibit the binding of the known compound is determined. For such assays, the known compound is labelled with a suitable detectible group, such as tritium. Other assays, such as gel mobility shift assays, may also be employed. The presence of binding to the site bound by ApoE3 indicates the compound is or may be useful for achieving one or more of the effects noted above. Compounds detected in this manner are useful for the in vitro and in vivo study of neurocellular degeneration and the treatment of Alzheimer's disease.

The present invention is explained in greater detail by the following Examples. These examples are illustrative of the present invention, and are not to be construed as limiting thereof.

EXAMPLE 1

ApoE3 Binds to Tau Protein

Recombinant tau-40 (the largest tau isoform in brain) was expressed and purified in accordance with known techniques (See M. Goedert et al., Neuron 3, 519 (1989)). ApoE was purified from individuals homozygous for ApoE3 or ApoE4, also in accordance with known techniques. (See S. Rall et al., Methods Enzymol. 128, 273 (1986)). The 22-kDa amino terminal fragment of ApoE3 or ApoE4 was prepared by thrombin cleavage (See W. Bradley et al., Biochem. Biophys. Res. Comm. 109,. 1360 (1982)). Tau-40 (2 $\mu$g protein) and ApoE (2 $\mu$g protein) were incubated in a total volume of 20 $\mu$l of phosphate buffered saline, Ph 7.30, for 60 min. at 37° C. The incubation was ended by adding 20 $\mu$l of 2×Laemmli buffer without $\beta$-mercaptoethanol (except lanes 9 and 10, which contained 0.2% $\beta$-mercaptoethanol V/V). The samples were heated in boiling water for 5 min. Proteins were electrophoretically separated on a 7.5% polyacrylamide gel and transferred to Immobilon P. The membrane was washed and incubated in primary antibody overnight in accordance with standard techniques. The primary antibody is a commercially available monoclonal anti-tau antibody (obtained from Boehringer Mannheim) diluted 1:2000 in Blotto (5% dried milk in Tris buffered saline, pH 7.6). After washing, the membrane was incubated with goat-anti-mouse F(ab')$_2$ conjugated with horseradish peroxidase (1:1500) for one hour. After washing, the horseradish peroxidase was visualized with an enhanced chemiluminescence detection kit (Amersham) and exposed to Hyperfilm ECL (Amersham) (see Y. Namba et al., Brain Res. 541, 163 (1991)).

Data are set forth in FIG. 1, which provides a demonstration of tau binding to ApoE3. Closed arrow indicates position of ApoE3/tau complex; Open arrow indicates position of 22-kDa amino-terminal fragment of ApoE/tau complex. Conditions for the various lanes are as follows: Lane 1) Tau-40 alone; Lane 2) Tau-40 and ApoE 3; Lane 3) Tau-40 and ApoE4; Lane 4) Tau-40 and 22 Kd amino-terminal fragment of ApoE3; Lane S) Tau-40 and 22-kDa fragment of ApoE4; Lane 6) Apo E3 alone; Lane 7) ApoE4 alone; Lane 8) Blank; Lane 9) Tau-40 and ApoE3, incubated and then boiled in Laemmli with β-mercaptoethanol; Lane 10) Tau-40 and ApoE4, incubated and then boiled in Laemmli with β-mercaptoethanol.

These data show that, in vitro, ApoE3 binds recombinant-expressed tau, forming a bi-molecular complex which resists dissociation by boiling in 2% sodium dodecyl sulfate. As shown in FIG. 1, the ApoE3/tau complex has an apparent molecular weight of approximately 105,000 daltons (tau-40 isoform in these experiments, 68,000 daltons; glycosylated ApoE, 39,000 daltons) and is not observed in either protein preparation alone. The binding of tau and ApoE3 is maximal within thirty minutes at 37° C. and is present between pH 7.6—4.6. The ApoE3/tau complex is destroyed by boiling with the reducing agent B-mercaptoethanol (FIG. 1).

EXAMPLE 2 AND 3

APoE4 Does Not Bind to Tau;

Neither ApoE3 nor ApoE4 Bind to Phosphorylated Tau

Figure 2A:
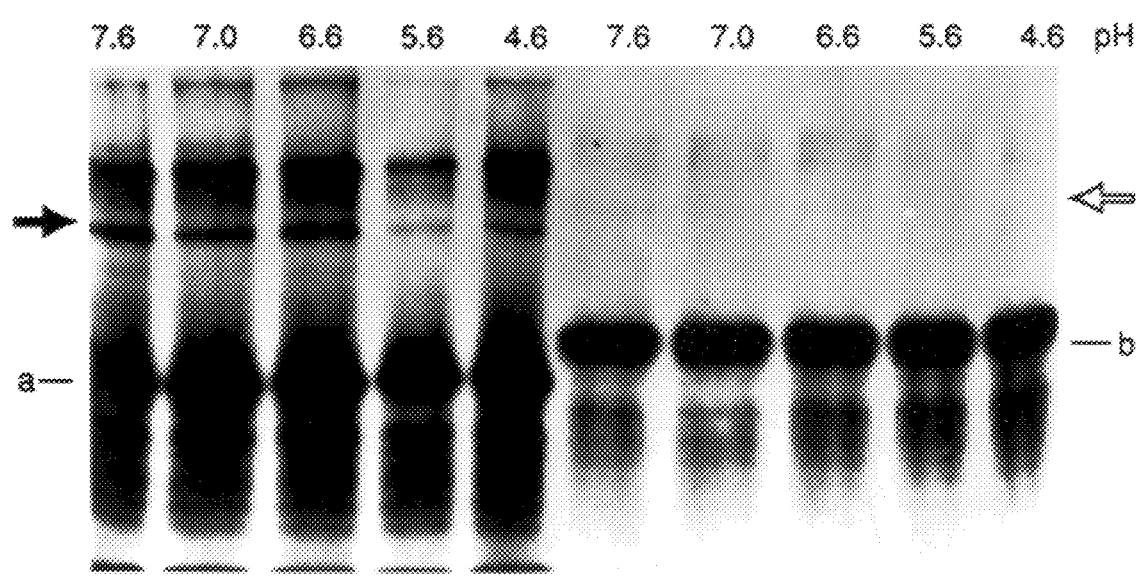
FIG. 2A illustrates the pH independent binding of tau to ApoE3 and the absence of binding of phosphorylated tau to ApoE3.
Figure 2B:
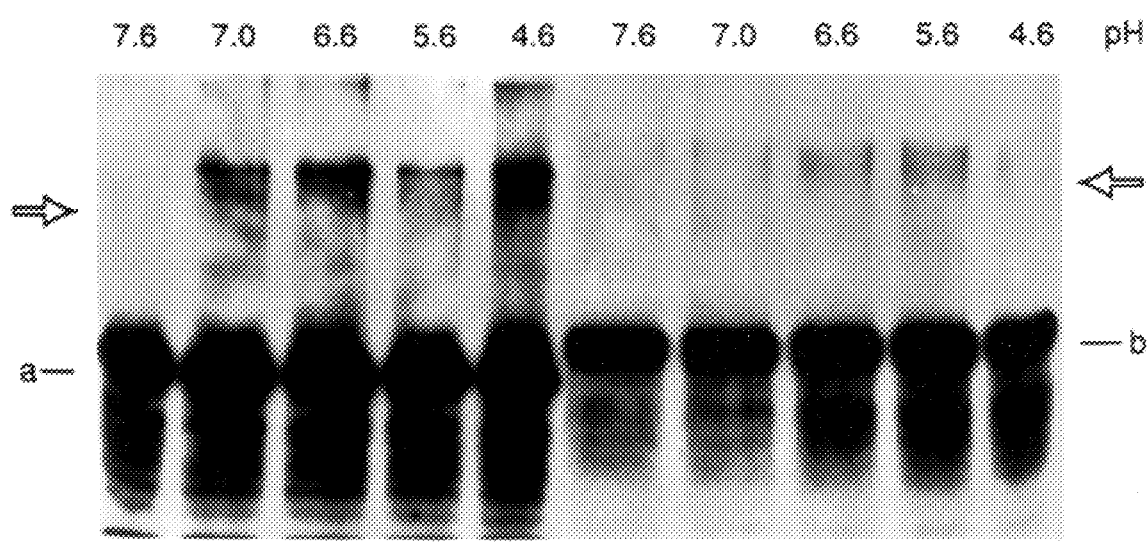
FIG. 2B illustrates the absence of tau binding to ApoE4 and the absence of binding of phosphorylated tau to ApoE4.

The pH independent binding of tau and ApoE3, the absence of tau binding with ApoE4, and the absence of binding of phosphorylated tau with either ApoE3 or ApoE4 are shown in FIG. 2A and FIG. 2B. ApoE3 (FIG. 2A) or ApoE4 (FIG. 2B) was incubated with either tau-40 (Lanes 1–5 in both FIG. 2A and FIG. 2B) or phosphorylated tau-40 (Lanes 6–10 in both FIG. 2A and FIG. 2B) in citric acid —$Na_2HPO_4$ buffer (6) at the indicated pH for 30 min at 37° C. The incubation was stopped as described in Example 1 above, the proteins were separated by electrophoresis and then transferred to Immobilon. Tau immunoreactive material was detected as described in Example 1 above. In FIG. 2A and 2B, closed arrow indicates position of ApoE3/tau complex, and open arrows indicate predicted positions of ApoE4/tau or ApoE/P-tau complexes. Phosphorylated tau was prepared by incubating recombinant tau-40 with homogenized brain supernatant, in accordance with known techniques (see J. Biernat et al., EMBO J. 11, 1593 (1992)). Note the slower migration of phosphorylated tau (Labelled b), compared with nonphosphorylated tau (Labelled a). FIGS. 2A and 2B, taken together, show that there is insignificant binding of tau by ApoE4 under a variety of conditions, including increased duration of incubation, increased concentration of ApoE4, or between pH 7.6—4.6.

In paired helical filaments, tau is abnormally phosphorylated at ser-pro and thr-pro sites (See N. Gustke et al., FEBS Letter 307, 199 (1992)). Recombinant tau can be phosphorylated at these sites by incubation with a crude rat brain extract in accordance with known techniques (see J. Biernat et al., supra.). Recombinant tau phosphorylated by this means was not bound by either ApoE3 or ApoE4, (FIGS. 2A and 2B) even with a prolonged twelve hour incubation.

EXAMPLE 4

Preparation of ApoE3 Fragments

The plasmid pTV 194, which expresses full-length ApoE3 in Escherichia coli (T. Vogel et al., Proc. Natl. Acad. Sci. USA 82, 8696–8700 (1985)), was modified to create four carboxyl-terminally truncated variants of ApoE3. These variants terminate at residues 266 (Glu), 244 (Glu), 223 (Ser) and 191 (Arg). They differ from native ApoE3 only in having an initial methionine at the amino terminus and in being carboxyl-terminally truncated. They are referred to as Met-$E_{266}$, Met-$E_{244}$, Met-$E_{223}$, and Met-$E_{191}$, respectively. The shortest variant, Met-$E_{191}$, is equivalent to the 22-kDa thrombin fragment of ApoE (Residues 1–191). The truncations were produced by introducing stop codons using mutagenic primers and the polymerase chain reaction to create DNA inserts that were ligated into pTV 194.

pu E. colistrain N4830-1 (Pharmacia LKB, Uppsala, Sweden) was transformed with the ligation products described above, and colonies on ampicillin plates were screened for the presence of inserts and for appropriate protein expression. The integrity of each construct was verified by double-stranded DNA sequencing (R. Kraft et al., BioTechniques 6, 544 (1988)). Human ApoE3 and its two major thrombolytic fragments were prepared in accordance with known techniques (T. Innerarity et al., J. Biol. Chem. 258, 12341 (1983); S. Rall et al., Methods Enzymol. 128, 273 (11986)). Truncated proteins were expressed and purified in accordance with standard techniques (See H. Yorie et al., J. Biol. Chem. 267, 11962 (1992)). Purified proteins were dialyzed into 100 mM $NH_4HCO_3$, quantitated by the method of Lowry (J. Biol. Chem. 193, 265 (1951)), and kept at −20° C. until use. The preparations were judged to be greater than 98% pure by sodium dodecyl sulfate-polyacrylamide gel electrophoresis (SDS-PAGE) run as previously described (J. Wetterau et al., J. Biol. Chem. 263, 6240 (1988)).

EXAMPLE 5

ApoE3 Fraqment Binding to Tau

Figure 3:
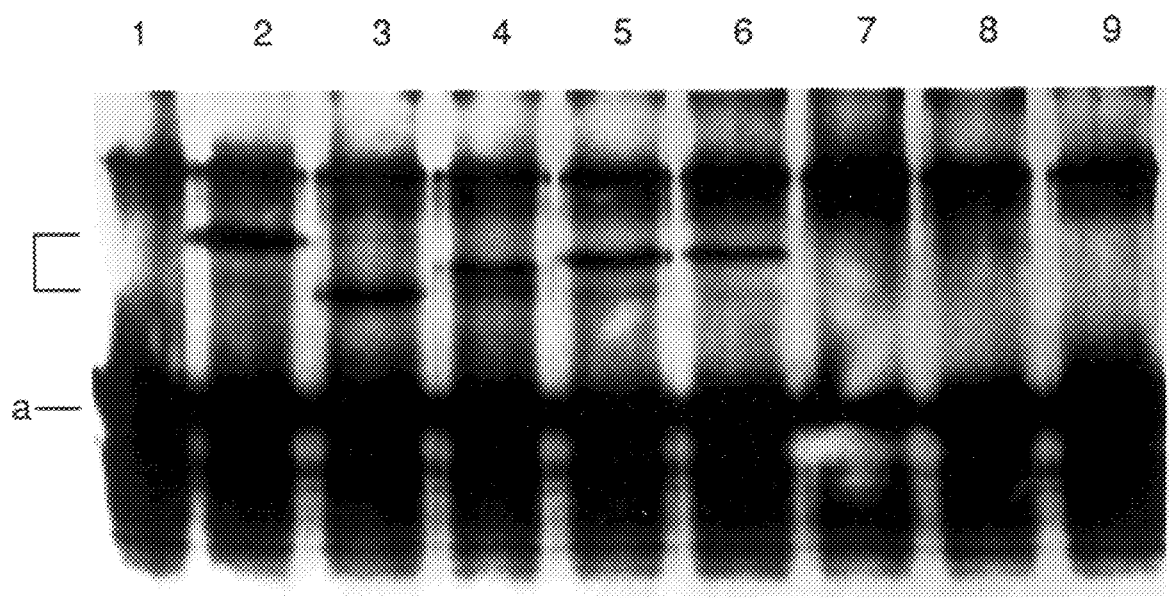
FIG. 3 illustrates the binding of various ApoE3 fragments to tau.

The binding of ApoE3 fragments to tau is shown in FIG. 3. Recombinant fragments of ApoE3 were prepared and purified as described in Example 4 above, and 2 μg protein was incubated with tau-40, as also described above. The arrow in FIG. 3 indicates tau-40, 68,000-kDa. Conditions in FIG. 3 are as follows: Lane 1) Tau-40 alone; Lane 2) Tau-40 and ApoE3 (native protein; amino acids 1–299): Lane 3) Tau-40 and 22-kDa amino-terminal fragment of ApoE3 (amino acids 1–191); Lane 4) Tau-40 and recombinant ApoE (amino acids 1–244); Lane 5) Tau-40 and recombinant ApoE (amino acids 1–266); Lane 6) Tau-40 and recombinant ApoE (amino acids 1–272); Lane 7) Tau-40 alone; Lane 8) Tau-40 and ApoE4 (native protein; amino acids 1–299); Lane 9) Tau-40 alone.

ApoE contains two functionally important domains, one which binds the LDL receptor and the other lipoprotein particles (VLDL or HDL). Thrombin cleaves ApoE at residues 191 and 215, yielding a 22-kDa amino-terminal fragment and a 10-kDa carboxyl-terminal fragment (W. Bradley et al., Biochem. Biophys Res. Comm. 109, 1360 (1982); T. Innerarity et al., supra). The receptor binding domain is located within the 22-kDa amino-terminal fragment and the 10-kDa fragment contains the lipid binding region of ApoE (N. Gustke et al., supra) and the region that binds the Aβ peptide. Tau binds to the 22-kDa amino-terminal fragment of ApoE3 (FIG. 1). Recombinant ApoE3 fragments, 1–244, 1–266, and 1–272, bind equivalent amounts of tau compared with that bound by the 22-kDa fragment (amino acids 1–191) (FIG. 3). Thus, tau binds the fragment of ApoE3 which also binds the LDL receptor, in a region distinct from the domain (between amino acids 245–272) that binds lipoprotein particles and the Aβ peptide. The 22-kDa aminoterminal fragment of ApoE4 does not bind tau (FIG. 1).

EXAMPLE 6

MAP2c Binds to ApoE3 But Not to APoE4

Rat MAP2c (see Kindler et al., J. Biol. Chem., 265, 19679 (1990)) was expressed in Escherichia coli by a modification of a known procedure (Goedert and Jakes, EMBO J., 9, 4225 (1990)). The MAP2c protein was purified by ion exchange chromatography on a Mono-S HR 5/5 column (Pharmacia) using a modification of the previously described procedure of Goedert and Jakes. Human apoE3 and apoE4 isoforms were isolated from subjects with the E3/3 and E4/4 homozygous phenotypes using known techniques (see Rall et al., Methods Enzymol., 128, 273 (1986)).

Figure 4:
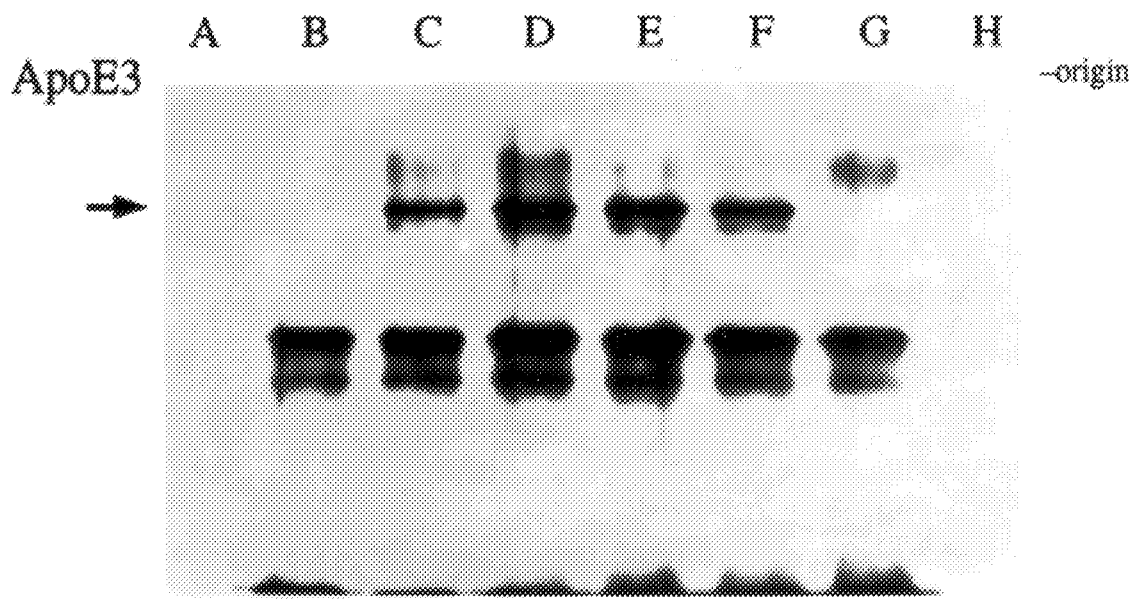
FIG. 4 illustrates the time-course of binding of MAP2c to apoE3; arrow indicates apoE3/MAP2c complex.
Figure 5:
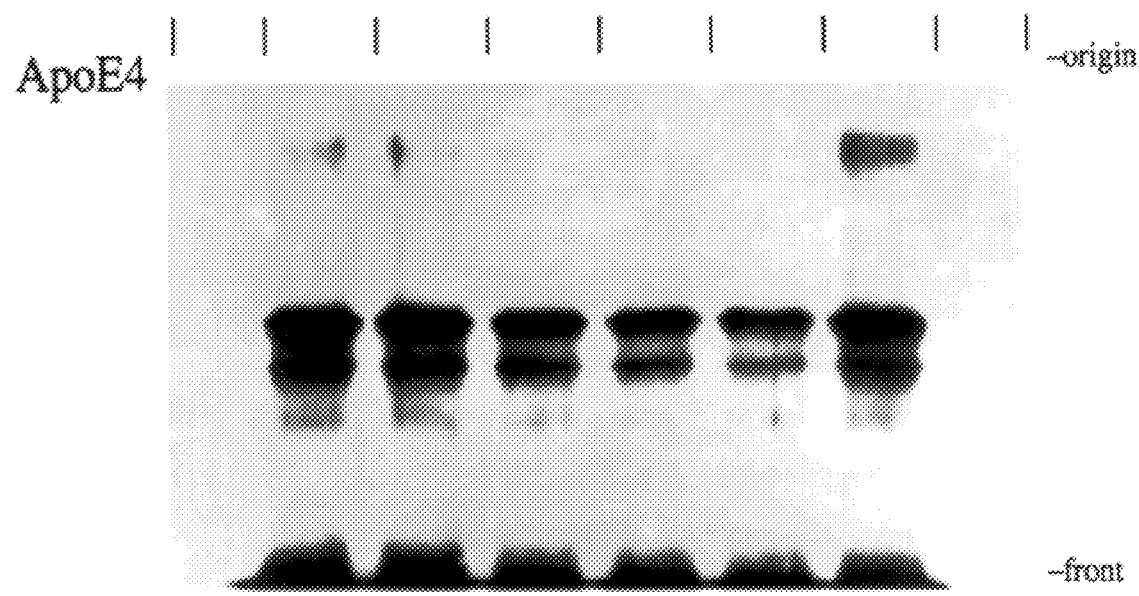
FIG. 5 illustrates the absence of binding of MAP2c to apoE4.

MAP2c (0.2 µg; final concentration of $3\times10^{-7}$ M) was incubated with 0.1 µg apoE3 or apoE4 (final concentration $3\times10^{-7}$ M) in a total volume of 10 µl in phosphate buffered saline (PBS), pH 7.30 at 37° C. for 1,2, or 4 hours. The incubation was ended by adding 10 µl of 2X Laemmli buffer (2% sodium dodecyl sulfate, without β-mercaptoethanol). Samples were heated in boiling water for 5 minutes. Proteins were electrophoretically separated on a 7.5% polyacrylamide gel and then transferred to a PVDF membrane (Millipore), as previously described (Strittmatter et al., Proc. Natl. Acad. Sci., 90, 8098 (1993)). The membrane was washed and incubated in antibody overnight in accordance with standard techniques. The primary antibody was a commercially available anti-MAP2 monoclonal antibody (obtained from Boehringer Mannheim), which detected the MAP2c-apoE complex. Binding of MAP2c to apoE3, forming a complex stable in sodium dodecyl sulfate, was detectable within 1 hour of incubation (FIG. 4; arrow indicates apoE3/MAP2c complex). However, no such binding of MAP2c by apoE4 was observed even after a 4 hour incubation (Lane E). FIG. 4 shows results of MAP2c and apoE3 incubation; results of MAP2c and apoE4 incubation are shown in FIG. 5. In FIG. 4 and FIG. 5, incubation with recombinant MAP2c occurred for 1 hour (Lane C); 2 hours (Lane D); 4 hours (Lane E); or 8 hours (Lane F). Lanes A and H contain ApoE and no MAP2c; Lanes B and G contain MAP2c and no apoE.

Figure 6:
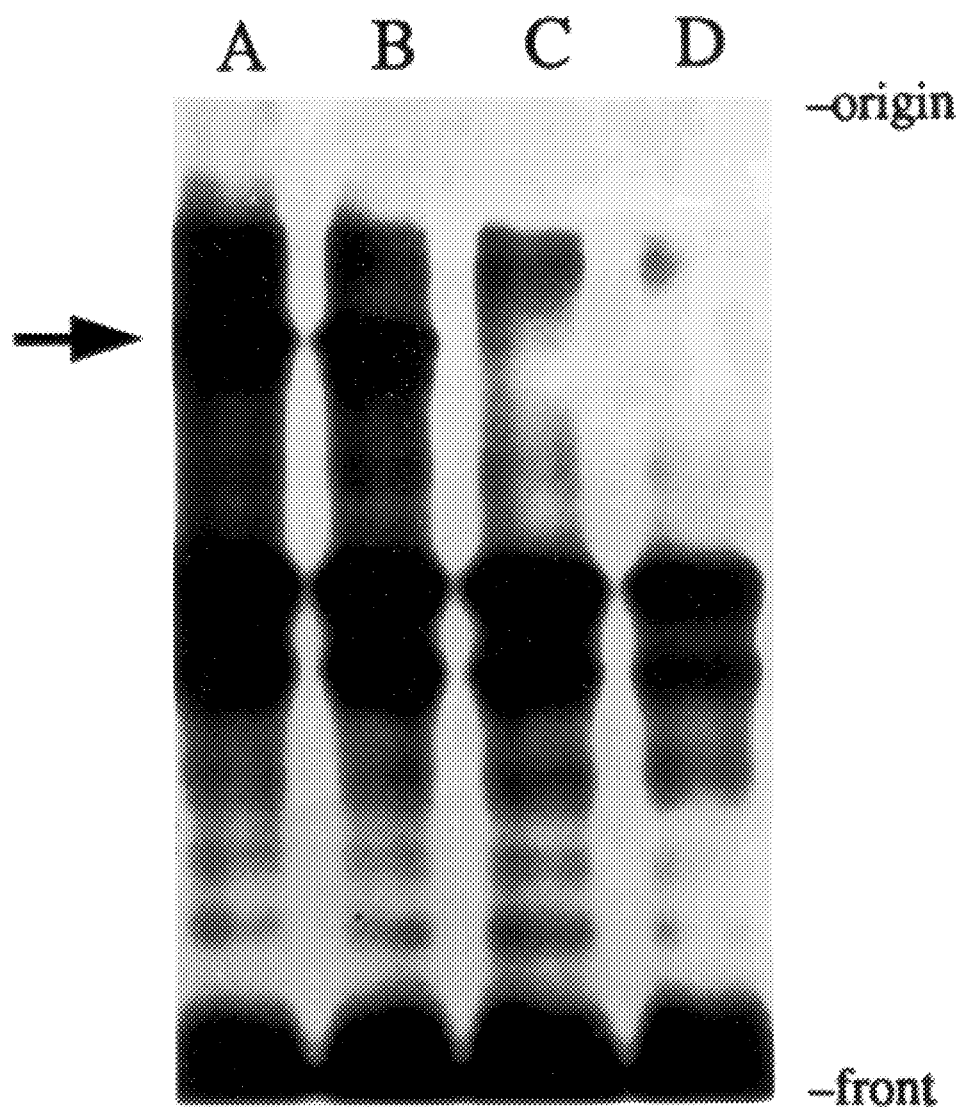
FIG. 6 illustrates the concentration dependence of apoE3 on binding of MAP2c. Arrow indicates apoE3/MAP2c complex.

To determine the lowest concentration of apoE3 detectably binding MAP2c, 0.2pg of MAP2c was incubated with 0.1, 0.01, or 0.001 µg (final concentrations of $3\times10^{-7}$, $3\times10^{-8}$, and $3\times10^{-9}$ M, respectively) of apoE3 in 10 µl PBS for 2 hours at 37° C. As seen in FIG. 6, the MAP 2c-apoE3 complex was still detectable at an apoE3 concentration of $3\times10^{-8}$ M. The amount of apoE3 bound increased with the concentration of apoE3. ApoE3 concentrations represented in FIG. 6 are: $3\times10^{-7}$M (Lane A); $3\times10^{-8}$ M (Lane B); and $3\times10^{-9}$M (Lane C). Lane D contained MAP2c and no apoE3. Arrow indicates apoE3/MAP2c complex.

Figure 7:
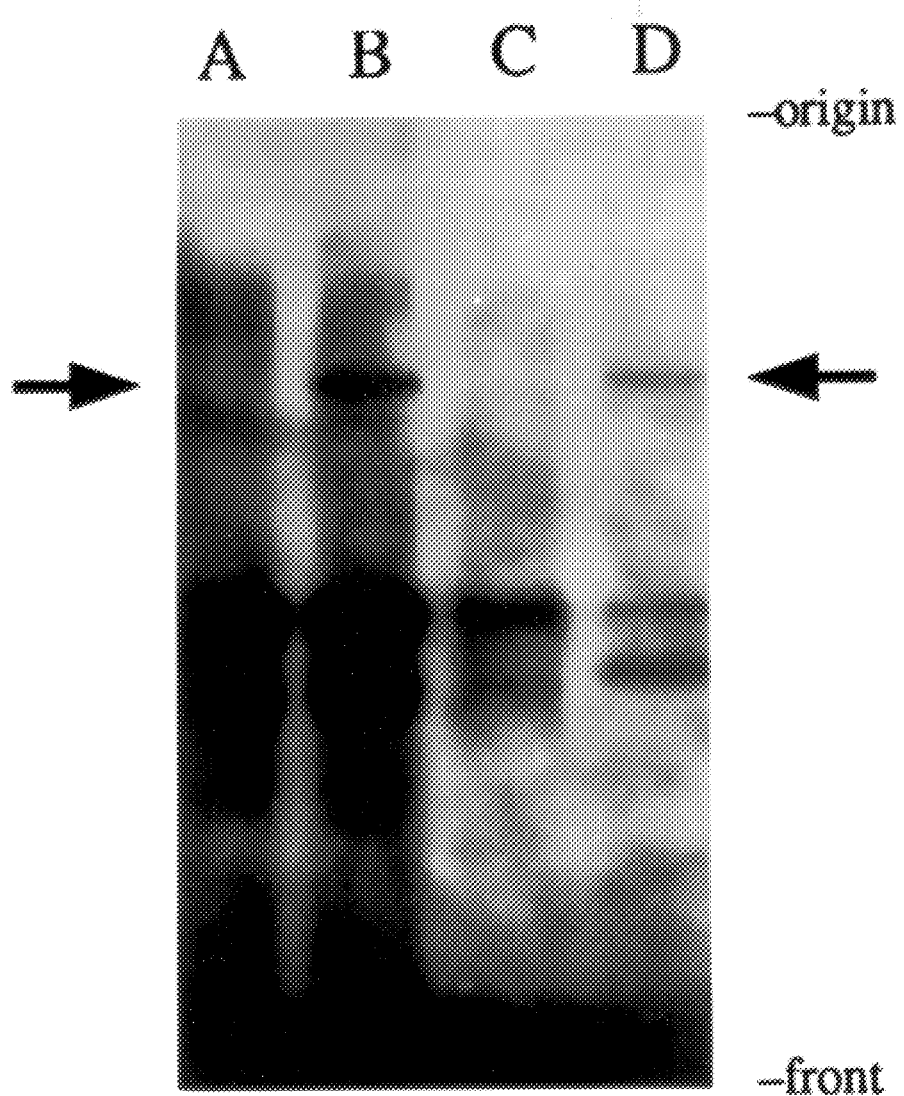
FIG. 7 illustrates the concentration dependence of MAP2c on binding of apoE3. Arrow indicates apoE3/MAP2c complex.

In a similar manner the lowest concentration of MAP2c binding to apoE3 was determined by incubating 0.1 µg of apoE3 with 0.2, 0.02, or 0.002 µg of MAP2c (final concentration of $3\times10^{-7}$, $3\times10^{-8}$, and $3\times10^{-9}$ M, respectively) in 10 µl of PBS for 2 hours at 37° C. Data set forth in FIG. 7 showed that the MAP2c-apoE3 complex was detectable at a MAP 2c concentration of $3\times10^{-9}$M. The amount of complex formed increased with MAP2c concentration. MAP2c concentrations represented in FIG. 7 are: $3\times10^{-8}$ M (Lanes A and B); $3\times10^{-9}$M (Lanes C and D). Lanes A and C contained no apoE3. Arrow indicates apoE3/MAP2c complex.

These results demonstrate that MAP2c binds apoE3 with high avidity, but does not bind apoE4. These results further support the generalized protective function of apoE3 binding to microtubule-associated proteins, including tau.

EXAMPLE 7

ApoE is Present in HippocamPal Neurons

Immunocytochemistry was used to compare apoE localization in the hippocampus of histologically-confirmed cases of Alzheimer's Disease (AD), Parkinson's Disease (PD) and normal controls (Han et al., Experimental Neurology, in press). ApoE localization was compared to Aβ-detected plaque and tau-detected tangle pathology.

Methods: Brains were collected from one to three hours after death from 24 AD patients, 5 patients with idiopathic PD without dementia, 8 PD patients with dementia (AD pathology) and six clinically examined non-demented patients who died of non-neurological disease. The 24 AD patients included each major ApoE genotype: APOE 3/3, APOE 3/4 and APOE 4/4. Pathological diagnoses were made by routine examination using techniques known in the art. The mid-hippocampal block with adjacent inferior temporal gyrus was used for immunocytochemical analysis. APOE genotyping for each patient was carried out as previously described using amplification by polymerase chain reaction (Saunders et al., Neurology, 43, 1467 (1993)).

Immunocytochemistry: Routine blocks of hippocampal region, frontal lobe and parietal lobe taken at autopsy were fixed for 5–7 days in 10% formalin and then embedded in paraffin for pathological analysis. 6–8 micron paraffin sections were cut and mounted on coated slides for immunocytochemistry. Sections were deparaffinized, treated with 90% formic acid for 3–5 minutes, washed and then incubated with specific antibodies for immunolocalization. Antibodies used were: rabbit polyclonal antibody to human apoE (1:5000 dilution) which demonstrates a single band on Western blots and reacts with all apoE isoforms (Strittmatter et al, Proc. Natl. Acad. sci. USA, 90, 1977 (1993) and Strittmatter et al., Proc. Natl. Acad. Sci. USA, 90, 8098 (1993)); mouse monoclonal "clone TAU-2" to bovine tau (1:1000 dilution, Leinco Technologies, St. Louis, Mo.) which recognized both phosphorylated and non-phosphorylated human tau (Binder et al., 1985); mouse monoclonal "Clone 10D5" to An 1–28 (Athena Neurosciences) which recognizes beta-pleated AP fragment (Hyman et al., J. Neuropath. Exp. Neurol., 51, 76 (1992)). Method controls with omission of primary antibody or substitution of other mouse monoclonal were included with each run. For apoE, pre-immune serum was run in parallel at the same concentrations as the post-immune primary antibody. Parallel controls were unstained. The tau antibody reliably and sensitively stained senile or neuritic plaques, neuropil threads, and neurons with presumptive neurofibrillary tangles or disordered cytoskeleton in patients with AD pathology.

Immunocytochemistry for apoE was performed on routine paraffin sections from the formalin-fixed hippocampal block for each of the above cases and combined with P-amyloid (AP) and tau immunocytochemistry to define senile plaque and neuronal pathology. Results reflect tightly bound apoE whose antigenicity was resistant to chemical fixation, extraction during fixation, dehydration, paraffin embedding, and dewaxing procedures, and furthermore resisted extraction during formic acid treatment.

Immunocytochemical Analysis: Several individuals observed sections from each case. Only sections from hippocampal region were used in analysis. Neurons reported as apoE immunoreactive were those that evidenced several fields containing immunoreactive neurons dark enough to be noticed with 10X objective (2.92 mm² field) and where cytological and immunochemical identification was positive at higher magnification. Adjacent sections analyzed for apoE-tau co-localization were examined by two observers using camera lucida and 20X objective. Each field was drawn out with appropriate landmarks and immunoreactive neurons were compared on each section.

Results in controls and non-demented PD patients: Results are shown in TABLE 1. ApoE immunoreactivity revealed staining of glial cells whose morphology resembled that of astrocytes, numerous small and larger cerebral vessels and often ependymal cells lining the hippocampal recess of the lateral ventricle. The most intense and consistent apoE immunostaining occurred in cerebral vessel walls (not shown). This staining included small parenchymal vessels as well as larger vessels adjacent to the ependymal border. Meningeal vessels were not usually strongly immunoreactive. ApoE immunoreactivity (apoE-IR) was also observed in the occasional senile plaque (SP) or amyloidotic vessel (inadequate to meet CERAD[1] criteria for AD diagnosis except in one case, see TABLE 1) which were easily detected with A# staining in adjacent sections. Apoe-IR was observed in glial cells presumed to be astrocytes by their size. In general the intensity of apoE immunoreactivity varied widely in brains of non-demented persons with four of the six cases having relatively faint staining of vessels and glial cells, barely above background controls.

[1]Consortium to Establish a Registry for Alzheimer's Disease (CERAD). See Mirra et al., Neurology, 41, 479 (1991).

ApoE immunoreactivity was found in hippocampal neurons of 2 of the six non-demented control brains. The brain of one patient (APOE 3/4) satisfied CERAD criteria for AD pathology for plaque counts but had essentially no neurofibrillary tangles (data not shown). The other normal control (APOE 3/3) had several fields of apoE-IR neurons.

ApoE immunoreactivity was found in five PD cases without dementia. Several fields of apoE immunoreactive hippocampal neuron were observed in each of the five patients. Glial and vascular staining similar to non-demented controls was also observed.

In the six non-demented normal controls and the five PD patients, apoE immunoreactive neurons clearly represented staining of neurons with no tau-immunoreactivity or neurofibrillary tangles. None of these 11 patients had appreciable tau-immunoreactive neurons present or neurons with neurofibrillary tangles detected during routine neuropathological exam.

ApoE in AD patients and demented PD patients: In all 24 AD cases, apoE immunoreactivity of cerebral vessels, glial cells presumed to be astrocytes, and hippocampal neurons was observed and was qualitatively similar to that seen in the non-demented controls. In addition to apoE immunoreactivity of senile plaques, amyloidotic vessels and neurons with neurofibrillary tangles as previously described were found (Strittmatter et al, Proc. Natl. Acad. Sci. USA, 90, 1977 (1993). No significant differences in apoE immunolocalization were found among the APOE genotypes, except for greater numbers of amyloidotic meningeal vessels and greater plaque densities in many APOE 4/4 cases as previously reported by Aβ immunolocalization (Schmechel et al., Proc. Natl. Acad. Sci. USA, 90, 9649 (1993)). Hippocampal sections from eight patients with PD and dementia (AD pathology) were also examined; ApoE immunolocalization in these eight cases resembled that observed in AD cases (TABLE 1).

TABLE 1

Clinical and Pathological Characteristics of Sample

| Clinical Diagnosis Group | No. Patients | Pathologic Diagnosis | APOE Genotype (number) | Average Age (range) | apoE (+) Hippocampal Neurons |
|---|---|---|---|---|---|
| Controls | 6 | 5 normal 1 AD | 3/3 (4) 3/4 (2) | 70 (59–86) | 2/6* |
| Alzheimers Disease (AD) | 24 | AD | 3/3 (6) 3/4 (10) 4/4 (8) | 77 (57–95) | 24/24 |
| Parkinsons Disease (PD) with dementia | 8 | PD, AD | 3/3 (1) 3/4 (5) 4/4 (2) | 75 (57–84) | 7/8 |
| Parkinsons Disease (PD) No dementia | 5 | PD | 3/3 (5) | 82 (73–87) | 5/5 |

*One normal control (APOE 3/4) with apoE immunoreactive neurons met CERAD criteria for plaques, but not tangles.
The other normal control with apoE immunoreactive neurons was APOE 3/3.

APoE immunoreactivity and Aβ-detected extracellular amyloid deposits: ApoE immunoreactivity generally correlated with Aβ immunoreactivity in adjacent sections including diffuse subpial deposits, amyloidotic vessels and senile plaques (data not shown). Strongly apoE immunoreactive amyloidoitic vessels were also Aβ immunoreactive in adjacent sections. In accord with previous reports (Strittmatter et al, Proc. Natl. Acad. Sci. USA, 90, 1977 (1993); Schmechel et al., Proc. Natl. Acad. Sci. USA, 90, 9649 (1993)), these results support a close correspondence between apoE and amyloid deposition.

ApoE immunoreactivity of vascular endothelial cells and glial cells: In contrast to controls, apoE immunoreactivity in AD brains was evident in association with both parenchymal and meningeal vessels. In addition to staining of capillaries and small vessels that was seen in controls, medium to large vessels in AD patients were often strongly immunoreactive to apoE antibody (data not shown). Extensive regions of apoE immunoreactive glial cells and cerebral vessels in both gray and white matter of hippocampus were common in AD patients of all apoE genotypes (data not shown). In some cases, intense isolated foci of apoE immunoreactive glial cells with the morphology of astrocytes could be observed near to and surrounding a single apoE-IR vessel (data not shown). The possibility that some of the immunoreactive glial profiles represented activated microglial cells could not be excluded, as in the control brains no positive cells with clearly microglial morphology were observed.

APoE immunoreactivity of neurites in senile plagues: ApoE immunocytochemistry of AD brains revealed numerous immunoreactive senile plaques (data not shown). With only rare exceptions, every apoE immunoreactive focus corresponded to an Aβ-immunoreactive plaque (data not shown). However, while apoE immunoreactivity consistently detected senile plaques, the character of apoE staining was not identical to AP immunoreactivity.

ApoE immunoreactivity of hippocampal neurons in AD patients: In the hippocampus of AD patients, apoE immunoreactive neurons were common in all patients (data not shown). The apoE immunoreactive neurons were present in variable numbers in all sectors of hippocampus and adjoining temporal cortex, including in some cases neurons of the granule cell layer of the dentate gyrus.

Relationship of apoE immunoreactive neurons to tau-detected neurofibrillary tangles: In many instances, the pattern of apoE immunoreactivity in some neurons clearly had the morphology of intracellular neurofibrillary tangles with linear, cytoplasm-distorting immunoreactive shape. However, more often, it was not immediately obvious that apoE and tau-immunoreactivity might be present in the same neuron except for the fact that the particular sector contained abundant numbers of separately identified apoE and tau immunoreactive neurons. ApoE-tau co-localization in adjacent sections of hippocampus stained for Aβ, tau and apoE immunolocalization was attempted. Hippocampal neurons were found that were both apoE immunoreactive and tau immunoreactive (data not shown). Other tau immunoreactive neurons were not stained in the adjacent apoE neuron. This data suggests that some apoE immunoreactive neurons are tau-immunoreactive in AD patients, but that apoE and tau immunoreactivity more commonly do not overlap under the conditions of this study (formaldehyde fixation, paraffin imbedding and dewaxing, formic acid treatment).

The overlap of apoE and tau immunoreactivity was also addressed by drawing with camera lucida the profiles of apoE and tau immunoreactive neurons in adjacent sections and comparing coincidents of staining. Counts of several fields in CA1–2 sector and in entorhinal cortex (ca. 380 neurons total) of a single patient revealed extensive numbers of apoE and tau immunoreactive pyramidal neurons in each field (10–40 tau-IR neurons/mm$^2$ and 10–40 apoE-IR neurons/mm$^2$ per field)(data not shown).

Discussion: The present study of apoE localization in human hippocampus and its relationship to AP and tau-defined AD pathology was designed to examine systematically whether (1) apoE is present in relevant cellular sites of AD pathology, and whether (2) the presence of apoE in neurons would support a direct and early role in neuronal pathology. The immunocytochemical results support the expected localization of apoE in astrocytes. Correlation with AP localization in AD patients confirms the close relationship of apoE to extracellular amyloid deposits in senile plaques and cerebral vessels. These findings indicate that apoE is not only present in the expected non-neuronal cell classes in the hippocampus of older humans—astrocytes, vascular endothelial cells, and ependymal cells—but is also present in hippocampal neurons without neurofibrillary changes. Intraneuronal apoE is not specific to AD, as apoE was also found in hippocampal neurons in two of six non-demented controls, as well as in thirteen brains from patients with Parkinson's disease with and without dementia. These findings indicate that apoE is present inside many "normal" hippocampal pyramidal neurons in older individuals and provides a possible basis for the effect of apoE on neuronal metabolism.

The results show that ApoE and tau immunoreactive neurons are numerous in affected sectors of hippocampus from AD patients, and that there may be significant overlap. The observation of apoE in neurons without neurofibrillary tangles in many normal controls and patients without AD suggests that apoE would be able to influence neuronal pathology of AD from the earliest time points. The above data indicates that neurofibrillary tangles may be a by-product of abnormal apoE/tau neuronal metabolism.

EXAMPLE 8

Apolipoprotein and Localization in cortical Neurons

Despite reports of apoE in neurons with neurofibrillary tangles (See, e.g., Strittmatter et al., Proc. Natl. Acad. Sci. USA, 90 1977 (1993), the presence of apoE in other neurons is still controversial. To determine subcellular distribution of apoE at the ultrastructural level, surgical specimens of human temporal lobe were obtained from five patients undergoing temporal lobectomy for medically intractable temporal lobe epilepsy. After fixation, sectioning and specific immunocytochemistry for apoE, the tissue was processed for light and electron microscopy. Inspection of this tissue in the electron microscope supported earlier light microscopic observations of human brains from patients with AD and aged controls: apoE was strongly localized in astrocytes and more weakly, but just as definitively, localized in neurons (Strittmatter et al., Proc. Natl. Acad. Sci. USA, 90 1977 (1993); Han et al., Exp. Neural (1994) (in press)). In glial cells, apoE immunoreactivity filled the perinuclear cytoplasm as well as distal processes. In neurons, apoE immunoreactivity was localized in a punctate fashion and was confined to the cell body. The presence of apoE in cortical neurons of AD patients, age-matched controls, and relatively young patients with epilepsy suggests that the astrocytic protein apoE may be commonly present in some cortical neurons. Furthermore, the localization of apoE to the cell body of neurons places it in a position to interact with the intraneuronal microtubule-associated protein, tau, and thus influence the rate of AD pathology (see Strittmatter et al., Exp. Neurol., 125 163 (1994)).

Tissue preparation: Blocks of temporal lobe tissue were obtained at the time of surgery from the temporal cortex of three male and two female medically intractable seizure patients ranging in age from 21 to 55 years, and at autopsy from one 77-year old male patient with Alzheimer's disease (AD) patient. Tissue was placed immediately in 4% paraformaldehyde in 0.1M phosphate buffer (pH 7.4). Soon thereafter, the blocks from each case were cut into two portions with one portion being left in 4% paraformaldehyde and the other transferred to a solution of 2% paraformaldehyde/0.2% glutaraldehyde in 0.1M phosphate buffer (pH 7.4). After immersion fixation for 24 hours at 4° C., both blocks were rinsed in 0.05M phosphate buffer with normal saline (PBS) and stored in 2% paraformaldehyde in 0.1M phosphate buffer (pH 7.4) until sectioning for immunocytochemistry.

Pre-embedding immunocytochemistry: Serial sections were cut on a Vibratome at 35–50 microns and collected free-floating in PBS. Sections were pretreated in freshly prepared 90% formic acid for 3–5 minutes or in 1% methanol-hydrogen peroxide for 5 minutes to enhance immunogenicity and to suppress endogenous peroxidase activity. After a series of 3 rinses in PBS for 5 minutes each, the sections were incubated for. 1 hour at room temperature and then overnight at 4° C. in a solution containing a mouse monoclonal antibody against human apoE (3H1, diluted 1:1000 in 2% normal goat serum). The 3H1 antibody was discovered using assays of inhibition of heparin-binding sites on apoE and recognizes amino acid residues 243–272 (Weisgraber et al., J. Biol. Chem., 261 2068 (1986)).

After 3 washes for 5 minutes each in PBS, tissue sections were then incubated for 30 minutes in biotinylated horse anti-mouse IgG (diluted 1:50, Vector Laboratories, Burlingame, Calif.) followed by washes and incubation for 30 minutes in avidin-biotin-peroxidase complex (Vector Laboratories).

Peroxidase activity was visualized by incubating the sections for 7–10 minutes in a solution containing 0.01% 3,3'-diaminobenzidine (DAB) and 0.0003% hydrogen peroxide in PBS. In order to rule out nonspecific binding and to ensure specificity, control reactions were carried out on adjacent sections with either omission of primary antiserum or replacement of the relevant secondary antibody by one raised in another species. After the DAB reaction, 35 micron sections were mounted on slides, dehydrated in a series of alcohols, cleared in xylene, and coverslipped. The 50 micron sections were processed for electron microscopy.

Electron microscopy: The 50 micron immunoreacted sections were postfixed in a solution of 1% osmium tetroxide in 0.1M phosphate buffer, dehydrated in a graded series of alcohols, and flat-embedded in Epon. After light microscopic observation of the cured sections, small areas containing apoE-immunoreactive neurons and glial cells were trimmed from the section, glued to a Epon post, and sections at approximately 50nm on a Reichert ultramicrotome. These sections were collected on formvar-coated grids with slots and left unstained for observation under JEOL 1200EX II electron microscope of 80 kV. Sections were examined and areas of interest were photographed at magnifications of 4,400–20,000 X for further analysis.

Light microscopy results: By light microscopy, apoE immunoreactivity was observed in sections taken from both the autopsy specimen of temporal lobe of the patient with AD and from the five surgical specimens of temporal lobe (data not shown). In both AD and temporal lobe epilepsy material, the pattern of immunoreactivity was specific to anti-apoE antibody and no staining was observed in control sections. In the AD case, plaques, many glial cells, and the pattern of immunoreactivity corresponded to previous observations in our laboratory of apoE localization in human brain specimens obtained at autopsy from 32 patients including normal controls, patients with AD, and patients with Parkinson's disease (Han et al., Exp. Neurol (1994) (in press)). In the surgical cases where no neuritic plaques or neurofibrillary tangles were observed, only glial cells and neurons were apoE immunoreactive (data not shown).

ApoE immunoreactivity was observed in tissue fixed in 2% paraformaldehyde/0.2% glutaraldehyde as well as in tissue fixed in 4% paraformaldehyde; however, apoE immunoreactivity was more robust in the tissue fixed in only paraformaldehyde. In these tissue blocks, the staining of astrocytic glial cells was particularly dense and complete; intense apoE immunoreactivity was present not only in the thin rim of cytoplasm surrounding the ,A nucleus but also in the processes as they spread throughout the neuropil and as they ended on blood vessels (data not shown). In contrast, the staining of neurons was less intense and confined to the region of cytoplasm just around the nucleus and in proximal processes (data not shown). Occasionally apo-E-immunoreactive satellite glial cells were observed in close proximity to labeled neurons.

Marked astrogliosis was observed in both the AD brain and the surgical temporal lobe specimens, and intense apoE staining of astrocytes was observed particularly in layer I and subcortical white matter. Stained glial cells included cells with morphology of protoplasmic and fibrillary astrocytes, as well as neuronal satellite glial cells. No apparent immunoreactivity of white matter oligodendrocytes was observed. Some staining of endothelial cells and blood vessel walls was observed. Some staining of endothelial cells and blood vessel walls was observed, and was attributed to heavy envelopment of astrocytic endfeet.

Electron microscopy results: Control sections reacted in parallel with omission of primary antibody were unstained at the light microscopic level (data not shown), and no immunoprecipitate was found in their companion thin sections at the ultrastructural level in any cell class (data not shown). In contrast, sections reacted with anti-apoE antibody revealed strongly stained glial cells at the light microscopic level (data not shown), and showed abundant profiles of heavily immunoreactive glial cells with dense HRP-reaction product filling their cell bodies and processes at the electron microscopic level (data not shown). Although immunoreactivity often decorated the external membranes of mitochondria, no specific compartmentalization of the reaction product was observed. Most structures were heavily immunolabeled, and labeling of other pertinent organelles such as Golgi vesicles or cisternae could not be ascertained. The same intense immunoreactivity of glial cell somas was also observed in numerous smaller processes in the surrounding neuropil. Based on the light microscope sections and on their intense immunoreactivity, these processes are probably smaller distal processes of immunoreactive glial cells. No associated synaptic densities or vesicles were observed in these processes. The strong immunoreactivity of astrocytes from soma to distal processes is supported by the staining of astrocytic endfeet that ended upon cerebral blood vessels which were heavily immunoreactive for their entire extent (data not shown).

Much of the neuropil was unstained in apoE immunoreacted sections. In particular, it was common to see large unstained areas of fine axonal and dendritic processes with occasional profiles of strongly immunoreactive, presumed astrocytic processes. Staining of neurons or neuropil in the control sections was not observed (data not shown). In apoE immunoreacted sections examined at the ultrastructural level, it was common to find neurons that contained no immunoreactivity in regions of neuropil that contained immunoreactive processes. However, as suggested by the companion sections prepared for light microscopy, some neurons were clearly apo-E-immunoreactive. In contrast to the glial cells, these neurons contained reaction product that was lighter and in punctate distribution (data not shown). As in glial cells, apoE-immunoreactivity was not confined to any particular subcellular compartment, but rather was present in clumps in the cytoplasm apparently associated with the membrane of the endoplasmic reticulum or other organelles and cellular structures. Heavy immunoprecipitate was seen on the outer membranes of structures with the appearance of microbodies as well as on mitochondria (data not shown); immunoprecipitate inside definite organelles or on the plasma or nuclear membrane was not seen. Unlike the situation for glial cells, no evidence for any immunoreactivity or any identified distal neuronal processes was found, whether axonal or dendritic, despite inspecting many fields with profiles of distal pre- and post-synaptic neuronal elements closely adjacent to heavily immunoreactive small processes presumed to be glial.

These results demonstrate the immuno-localization of apoE in cortical neurons as well as in glial cells. The additional light and electron microscopic evidence for neuronal localization of apoE is in contrast to the commonly held viewpoint that apoE is localized only in astrocytes and glial cells (see, e.g., Rebeck et al., Neuron 11 575 (1993)). Most previous studies on the immunolocalization of apoE have been carried out in rodent brain and have reported the presence of apoE in glial cells and particularly astrocytes. An astrocytic localization for apoE fits with the observation that apoE mRNA is found only in glial cells and not in neurons in the central nervous system.

The present results demonstrate that (a) apoE is in the cell body region of many cortical neurons, (b) apoE is present in the cytoplasm, (c) apoE is often associated with the external membrane surface of some, but not all, intracellular organelles, and (d) the apparent content of apoE in neurons is less abundant than in glial cells.

The failure to observe neuronal localization of apoE in other studies could be due to: immunoreagents employed, loss of antigen/alteration of antigen during fixation and processing, and species or individual differences in apoE localization.

Finally, most studies reporting absence of apoE in neurons have been performed in rodents. We find that apoE is rarely localized in cortical neurons in rodents, often only in older specimens (work in preparation). As described in Example 7, in normal human aged controls, localization of apoE in hippocampal neurons was found in 2 of 6 cases, and neuronal apoE localization was found in essentially all cases of AD and PD.

These results indicate that apoE is involved directly with neuronal function and is in a position to interact with the microtubule associated protein, tau.

The foregoing examples are illustrative of the present invention, and are not to be construed as limiting thereof. The invention is defined by the following claims, with equivalents of the claims to be included therein.

That which is claimed is:

1. A method of screening a test compound for the ability to bind tau protein at the tau protein binding site for ApoE3, comprising detecting whether said test compound inhibits binding of ApoE3 to tau protein.

2. A method according to claim 1, wherein said contacting step is carried out in vitro.

3. A method of screening a test compound for the ability to bind tau protein at the tau protein binding site for ApoE3, comprising:

(a) contacting a test compound to tau protein;
    (b) contacting ApoE3 to said tau protein; and
    (c) detecting whether said test compound inhibits binding of ApoE3 to said tau protein, compared to that which would occur in the absence of said test compound.

4. A method according to claim 3, wherein said contacting step is carried out in vitro.

5. A method of screening a test compound for the ability to bind tau protein at the tau protein binding site for ApoE2, comprising detecting whether said test compound inhibits binding of ApoE2 to tau protein.

6. A method of screening a test compound for the ability to bind tau protein at the tau protein binding site for ApoE2, comprising:

(a) contacting a test compound to tau protein;
    (b) contacting ApoE2 to said tau protein; and
    (c) detecting whether said test compound inhibits binding of ApoE2 to said tau protein, compared to that which would occur in the absence of said test compound.

* * * * *

UNITED STATES PATENT AND TRADEMARK OFFICE
CERTIFICATE OF CORRECTION

PATENT NO. : 5,811,243
DATED : September 22, 1998
INVENTOR(S) : Warren J. Strittmatter, Allen D. Roses, Michel Goedert, Karl H. Weisgraber, Ann M. Saunders, Donald E. Schmechel It is certified that error appears in the above-identified patent and that said Letters Patent is hereby corrected as shown below:

On the title page, item [54] and column 1, lines 1-2, replace

"Methods and Compositions for Binding TAU and MAP2C Proteins"
with --Methods of Screening Compounds for the Ability to Bind TAU or MAP2c--.

Signed and Sealed this

Sixteenth Day of March, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,811,243
DATED : 22 September 1998
INVENTOR(S) : Warren J. Strittmatter, Allen D. Roses, Michel Goedert, Karl H. Weisgraber, Ann M. Saunders, Donald E. Schmechel It is certified that error appears in the above-identified patent and that said Letters Patent is hereby corrected as shown below:

On the title page, item [73] and column 1, please add the following assignees:

--Medical Research Council, London, England--
--The Regents of the University of California, Oakland, CA---

Signed and Sealed this

Twenty-eighth Day of December, 1999

Attest:

Attesting Officer

Q. TODD DICKINSON

Acting Commissioner of Patents and Trademarks